United States Patent
Paysan et al.

(10) Patent No.: US 10,524,756 B2
(45) Date of Patent: Jan. 7, 2020

(54) METHODS AND SYSTEMS FOR IMAGE ARTIFACTS REDUCTION

(71) Applicant: VARIAN MEDICAL SYSTEMS INTERNATIONAL AG, Cham (CH)

(72) Inventors: Pascal Paysan, Basel (CH); Luis Melo De Carvalho, Affoltern am Albis (CH); Dieter Seghers, Zurich (CH); Marcus Brehm, Zurich (CH)

(73) Assignee: VARIAN MEDICAL SYSTEMS INTERNATIONAL (CH)

( * ) Notice: Subject to any disclaimer, the term of this patent is extended or adjusted under 35 U.S.C. 154(b) by 279 days.

(21) Appl. No.: 14/838,352

(22) Filed: Aug. 27, 2015

(65) Prior Publication Data
US 2017/0055931 A1    Mar. 2, 2017

(51) Int. Cl.
| | |
|---|---|
| *G06K 9/00* | (2006.01) |
| *A61B 6/00* | (2006.01) |
| *A61B 6/03* | (2006.01) |
| *G06T 7/00* | (2017.01) |
| *G06T 11/00* | (2006.01) |

(52) U.S. Cl.
CPC ............ *A61B 6/5264* (2013.01); *A61B 6/032* (2013.01); *A61B 6/4085* (2013.01); *G06T 7/0012* (2013.01); *G06T 11/005* (2013.01); *G06T 11/008* (2013.01); *G06T 2207/10081* (2013.01); *G06T 2211/432* (2013.01)

(58) Field of Classification Search
None
See application file for complete search history.

(56) References Cited

U.S. PATENT DOCUMENTS

| | | | |
|---|---|---|---|
| 4,580,219 | A | 4/1986 | Pelc et al. |
| 4,590,558 | A | 5/1986 | Glover et al. |
| 2002/0154735 | A1 | 10/2002 | Simon et al. |
| 2006/0262894 | A1 | 11/2006 | Bernhardt et al. |
| 2008/0240335 | A1 | 10/2008 | Manjeshwar et al. |
| 2008/0285711 | A1 | 11/2008 | Avinash et al. |

(Continued)

FOREIGN PATENT DOCUMENTS

| | | |
|---|---|---|
| WO | 2008099314 A2 | 8/2008 |
| WO | 2008099314 A3 | 8/2008 |

OTHER PUBLICATIONS

K. Sourbelle et al., "Reconstruction from Truncated Projections in CT Using Adaptive Detruncation", Eur Radial, 2005, pp. 1008-1014, vol. 15.

(Continued)

*Primary Examiner* — Sean M Conner
(74) *Attorney, Agent, or Firm* — SU IP Consulting

(57) ABSTRACT

One example method to reduce image artifacts, which may include obtaining measured projection data acquired using an imaging system. The measured projection data is associated with a target object and an artifact source within a radiation field of the imaging system. The method may also include generating virtual projection data associated with the artifact source by forward projecting a model representing one or more physical properties of the artifact source. The method may further include generating corrected projection data based on the measured projection data and the virtual projection data; and reconstructing the corrected projection data into reconstructed volume image data to reduce image artifacts caused by the artifact source.

9 Claims, 9 Drawing Sheets

(56) References Cited

U.S. PATENT DOCUMENTS

2011/0081071 A1 4/2011 Benson et al.
2015/0078507 A1 3/2015 Yiannis

OTHER PUBLICATIONS

International Search Report and Written Opinion of the International Searching Authority, International application No. PCT/US2016/049148, dated Oct. 28, 2016.
The Extended European Search Report, Application No. 16840243.6, dated Mar. 4, 2019.
Jakob Toftegaard et al., "Moving Metal Artifact Reduction in Cone-Beam CT Scans with Implanted Cylindrical Gold Markers", Medical Physics, Dec. 2014, pp. 121710-1-121710-8, No. 12, vol. 14.

METHODS AND SYSTEMS FOR IMAGE ARTIFACTS REDUCTION

BACKGROUND

Unless otherwise indicated herein, the approaches described in this section are not prior art to the claims in this application and are not admitted to be prior art by inclusion in this section.

Computerized tomography (CT) involves the imaging of the internal structure of a target object by collecting projection data in a single scan operation ("scan"). CT is widely used in the medical field to view the internal structure of selected portions of the human body. In an ideal imaging system, rays of radiation travel along respective straight-line transmission paths from the radiation source, through a target object, and then to respective pixel detectors of the imaging system to produce volume data (e.g., volumetric image) without artifacts.

However, in practice, volume data may contain image artifacts, such as streaking, noise, cupping, ringing, shadows, blurring, etc. For example, the image artifacts may be caused by errors in the projection data, such as data inconsistencies, missing data, geometrical uncertainties, superimposition in the projection space, various physical properties (e.g., scatter not covered by the reconstruction algorithm), etc. All of the foregoing leads to image degradation and affects, for example, subsequent diagnosis and treatment planning. It is therefore desirable to develop techniques that reduce image artifacts in the volume data by correcting the projection data.

SUMMARY

In at least one example of the present disclosure, there is disclosed a method to reduce image artifacts. The method may include obtaining measured projection data acquired using an imaging system, the measured projection data being associated with a target object and an artifact source within a radiation field of the imaging system. The method may also include generating virtual projection data associated with the artifact source by forward projecting a model representing one or more physical properties of the artifact source. The method may further include generating corrected projection data based on the measured projection data and the virtual projection data; and reconstructing the corrected projection data into reconstructed volume image data to reduce image artifacts caused by the artifact source.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
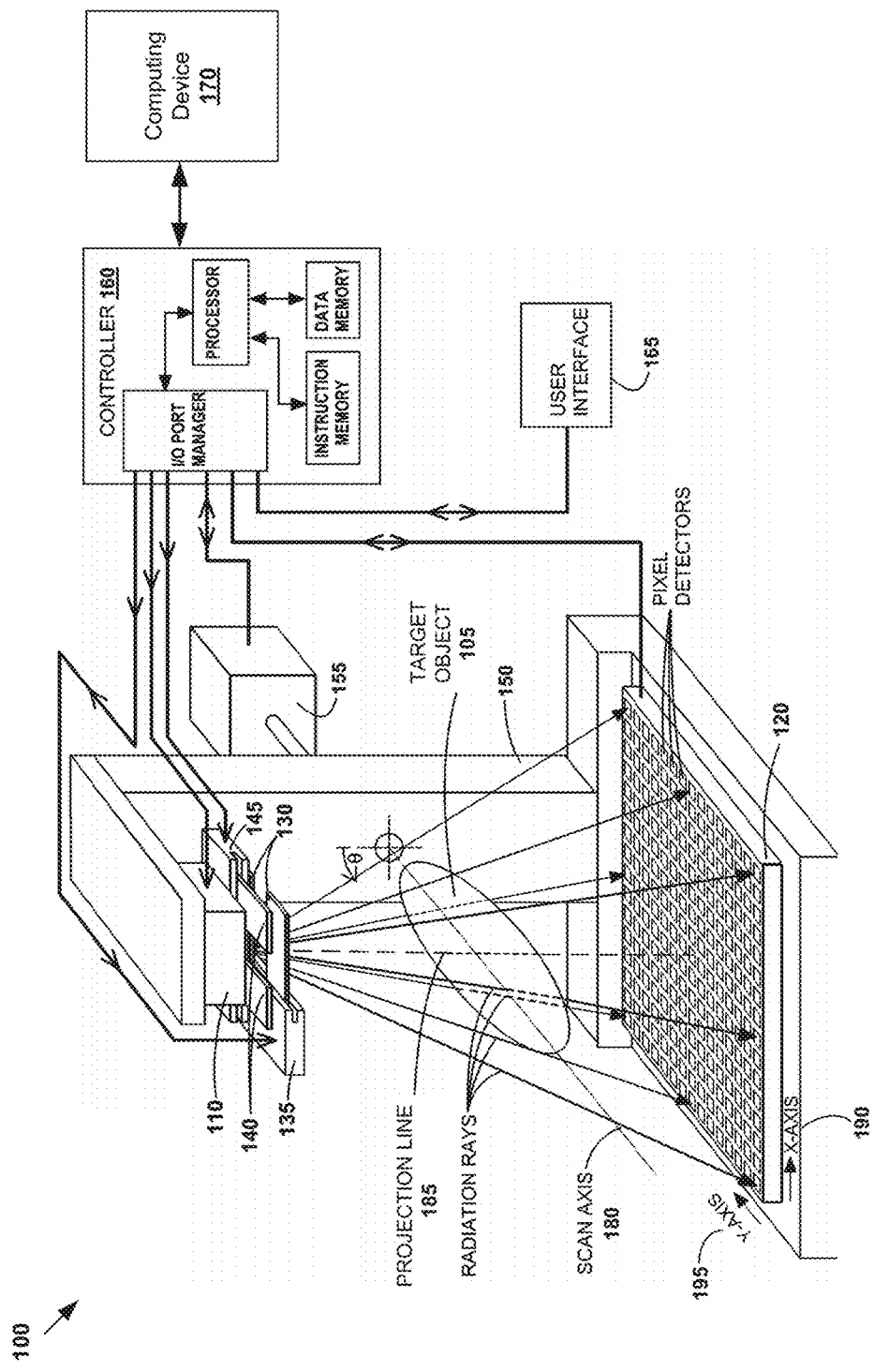
FIG. 1 is a schematic diagram illustrating an example imaging system.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

FIG. 1 is a schematic diagram illustrating example imaging system 100. Although one example is shown, imaging system 100 may have alternative or additional components depending on the desired implementation in practice. In the example FIG. 1, imaging system 100 includes radiation source 110; detector 120 having pixel detectors disposed opposite to radiation source 110 along a projection line (defined below; see 185); first set of fan blades 130 disposed between radiation source 110 and detector 120; and first fan-blade drive 135 that holds fan blades 130 and sets their positions. The edges of fan blades 130 may be oriented substantially perpendicular to a scan axis (defined below; see 180), and are substantially parallel with the trans-axial dimension (defined below) of detector 120.

Imaging system 100 may further include second set of fan blades 140 disposed between radiation source 110 and detector 120, and second fan-blade drive 145 that holds fan blades 140 and sets their positions. The edges of fan blades 140 may be oriented substantially parallel with a scan axis (defined below; see 180), and are substantially perpendicular to the axial dimension (defined below) of detector 120. Fan blades 130 and 140 are generally disposed closer to the radiation source 110 than detector 120. They are normally kept wide open to enable the full extent of detector 120 to be exposed to radiation, but may be partially closed in certain situations.

Imaging system 100 further includes gantry 150 that holds at least radiation source 110, detector 120, and fan-blade drives 135 and 145 in fixed or known spatial relationships to one another, mechanical drive 155 that rotates gantry 150 about target object 105 disposed between radiation source 110 and detector 120, with target object 105 being disposed between fan blades 130 and 140 on the one hand, and detector 120 on the other hand. The term "gantry" has a broad meaning, and covers all configurations of one or more structural members that can hold the above-identified components in fixed or known (but possibly movable) spatial relationships. For the sake of visual simplicity in the figure, the gantry housing, gantry support, and fan-blade support are not shown.

Additionally, imaging system 100 includes controller 160, user interface 165, and computing device 170. Controller 160 may be electrically coupled to radiation source 110, mechanical drive 155, fan-blade drives 135 and 145, detector 120, and user interface 165. User interface 165 may be configured to enable a user to at least initiate a scan of target object 105, and to collect measured projection data from detector 120. User interface 165 may be configured to present graphic representations of the measured projection data. Computing device 170, coupled to controller 160, may be configured to perform simulation operations, data processing operations, and other operations that will be described in more detail below.

In imaging system 100, gantry 150 may be configured to rotate about target object 105 during a scan such that radiation source 110, fan blades 130 and 140, fan-blade drives 135 and 145, and detector 120 circle around target object 105. More specifically, gantry 150 may rotate these components about scan axis 180. As shown in FIG. 1, scan axis 180 intersects with projection line 185, and is typically perpendicular to projection line 185. Target object 105 is generally aligned in a substantially fixed relationship to scan axis 180. The construction provides a relative rotation between projection line 185 on one hand, and scan axis 180 and target object 105 aligned thereto on the other hand, with the relative rotation being measured by an angular displacement value θ.

Mechanical drive 155 may be coupled to the gantry 150 to provide rotation upon command by controller 160. The array of pixel detectors on detector 120 may be periodically read to acquire the data of the radiographic projections (also referred to as "measured projection data" below). Detector 120 has X-axis 190 and Y-axis 195, which are perpendicular to each other. Detector 120 may be oriented such that its Y-axis 195 is parallel to scan axis 180. For this reason, Y-axis 195 may also be referred to as the axial dimension of detector 120, and X-axis 190 may be referred to as the trans-axial dimension, or lateral dimension, of detector 120.

X-axis 190 is perpendicular to a plane defined by scan axis 180 and projection line 185, and Y-axis 195 is parallel to this same plane. Each pixel on detector 120 is assigned a discrete X-coordinate ("X") along X-axis 190 and a discrete Y-coordinate ("Y") along the Y-axis 195. A smaller number of pixels are shown in the figure for the sake of visual clarity. Detector 120 may be centered on projection line 185 to enable full-fan imaging of target object 105, may be offset from projection line 185 to enable half-fan imaging of target object 105, or may be movable with respect to projection line 185 to allow both full-fan and half-fan imaging of target object 105.

Throughout the present disclosure, the terms "projection view", and "projection angle" are used interchangeably. The terms "projection data", "projection(s)", "radiographic projection(s)" and "projection image(s)" are also used interchangeably.

Figure 2:
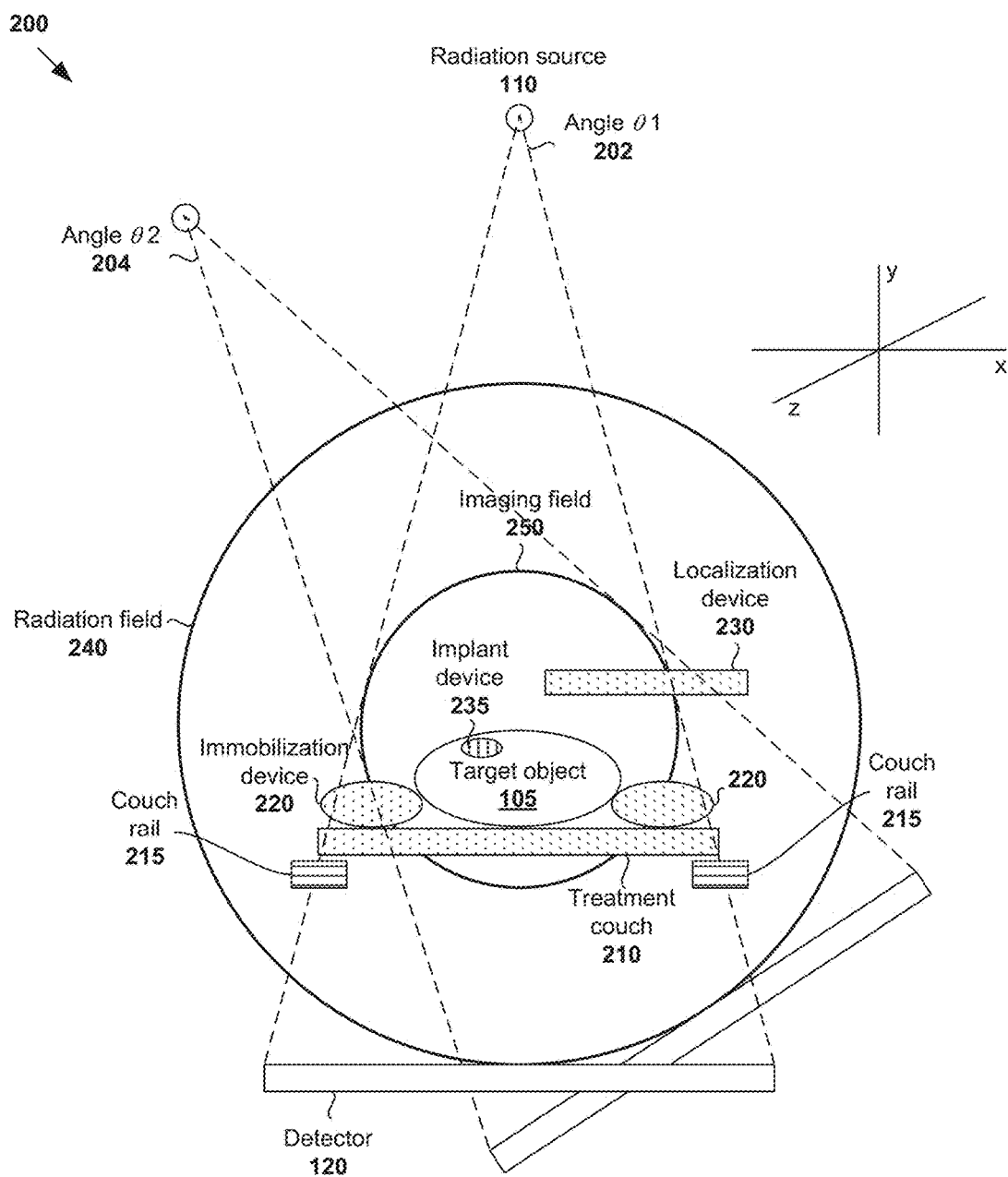
FIG. 2 is a schematic diagram illustrating an example configuration of a radiation source and a detector with respect to a target object at multiple projection angles.

As explained using FIG. 1, radiation source 110 and detector 120 may be rotated 360° about target object 105 to acquire projection data at various angles, such as for every 1°. In more detail, FIG. 2 is a schematic diagram illustrating example configuration 200 of radiation source 110 and detector 120 with respect to target object 105 at multiple projection angles. The X-Y plane is defined as the plane of the paper and the Z axis extends out from the paper. For simplicity, two projection angles θ1 (see 202) and θ2 (see 204) are shown in FIG. 2 but projection data may be collected at additional or alternative angles in practice.

During imaging, target object 105 (generally a patient, etc.) lies on a patient table or treatment couch 210 (e.g., having couch rails 215) while radiation source 110 is rotated about target object 105. Target object 105 is also generally held at a relatively stationary position using immobilization device 220, such as a head mask, neck mask, headrest, head frame, body-fix frame, eye and chin mask, bite blocks, upper bite mold, patient support frame, vacuum mold bags, polyurethane foam casts, etc. To facilitate real-time tracking of a structure or region of interest (e.g., tumor) of target object 105, localization device 230 such as the Calypso system from Varian Medical Systems, Inc., etc., may be used. This enables clinician to keep the region of interest in the path of radiation beam from radiation source 110 substantially at all times. In practice, the Calypso system may perform real-time tracking using radiofrequency waves. Target object 105 may be implanted with at least one electromagnetic transponder (see implant 235) to transmit location information to localization device 230.

In a cone-beam computerized tomography (CBCT) system, various components may scatter radiation and introduce artifacts. Some examples include, without limitation, a bow-tie filter, the target object being scanned, an anti-scatter grid, and the detector housing of the system. Additional description is provided in a commonly owned U.S. Pat. No. 8,326,011, which is incorporated by reference herein in its entirety.

Further, treatment couch 210, couch rails 215, immobilization device 220, localization device 230 and implant device 235 may cause considerable image artifacts in reconstructed image data generated from projection data acquired using imaging system 100. For example, treatment couch 210 may introduce beam hardening and scatter, and movement of treatment couch 210, couch rails 215, immobilization device 220, localization device 230 and implant device 235 during scanning may also cause motion artifacts (e.g., streaking, blurring, etc.) in the reconstructed volume data.

Truncation may also be evident in the projection space due to missing data. Such truncation mainly results in cupping artifacts (commonly known as truncation artifacts) in the volume space if not handled properly. In the example in FIG. 2, truncation may occur when treatment couch 210, immobilization device 220 and localization device 230 are located within radiation field 240 (also known as "radiated field") of imaging system 100, but not fully covered by imaging field 250. Truncation may also occur when couch rails 215 or any other device are located within radiation field 240, but outside of imaging field 250. This is because imaging field 250 is generally smaller than radiation field 240 due to limitations of imaging system, such as the size of detector 120. Since imaging field 250 represents a field of measurement of imaging system 100, any object that is not fully irradiated, because it is fully or partially outside imaging field 250, will only be partially visible or not visible in the projection data.

As an example, since treatment couch 210 is not fully within imaging field 250, some data relating to treatment couch 210 (e.g., edges that extend beyond imaging field 250) will be missing when radiation source 110 is at certain positions or angles (e.g., due to the size of detector 120). In this case, parts of treatment couch 210 that are within imaging field 250 are visible in all projection data. However, other parts of treatment couch 210 that are outside of imaging field 250 may be included at certain view angles and may not be included for other view angles. This is also known as the missing data issue and causes data inconsistencies in the projection data. In practice, the amount of truncation may depend on the size of detector 120; the size of couch 210, couch rails 215, immobilization device 220 or localization device 230 and the projection angle of radiation source 110, etc. Truncation may become evident in the projection space due to missing data next to the edge of detector 120.

In another example, implant device 235 that is fully within both radiation field 240 and imaging field 250 may also cause scatter in the projection data that results in undesirable image artifacts in the reconstructed image volume. The image artifacts reduce the quality of the reconstructed volume image data, which in turn adversely affects the quality of any subsequent diagnosis, patient positioning, treatment planning, dose verification, or any other analysis that relies on the reconstructed volume data. In the following, the term "artifact source" will be used to refer generally to an object, device or system located within radiation field 240 that introduces errors (e.g., data inconsistencies, missing data, scatter, etc.) in the projection data acquired during a scan and in turn causes image artifacts in the volume data reconstructed from the projection data.

The artifact source may be (a) fully visible, (b) partially visible or (c) not visible within imaging field 250. These scenarios are represented in FIG. 2 at (a) 260 (i.e., fully within imaging field 250), (b) 261 (i.e., partially within imaging field 250) and (c) 262 (i.e., outside of imaging field 250), respectively. Although treatment couch 210, couch rails 215, immobilization device 220, localization device 230 and implant device 235 are used as examples in FIG. 2, the model-based approach may be used for other artifact sources such as implant devices for other purposes, fiducial markers, etc. In some cases, target object 105 itself may be an artifact source.

Image Artifact Reduction

Figure 3:
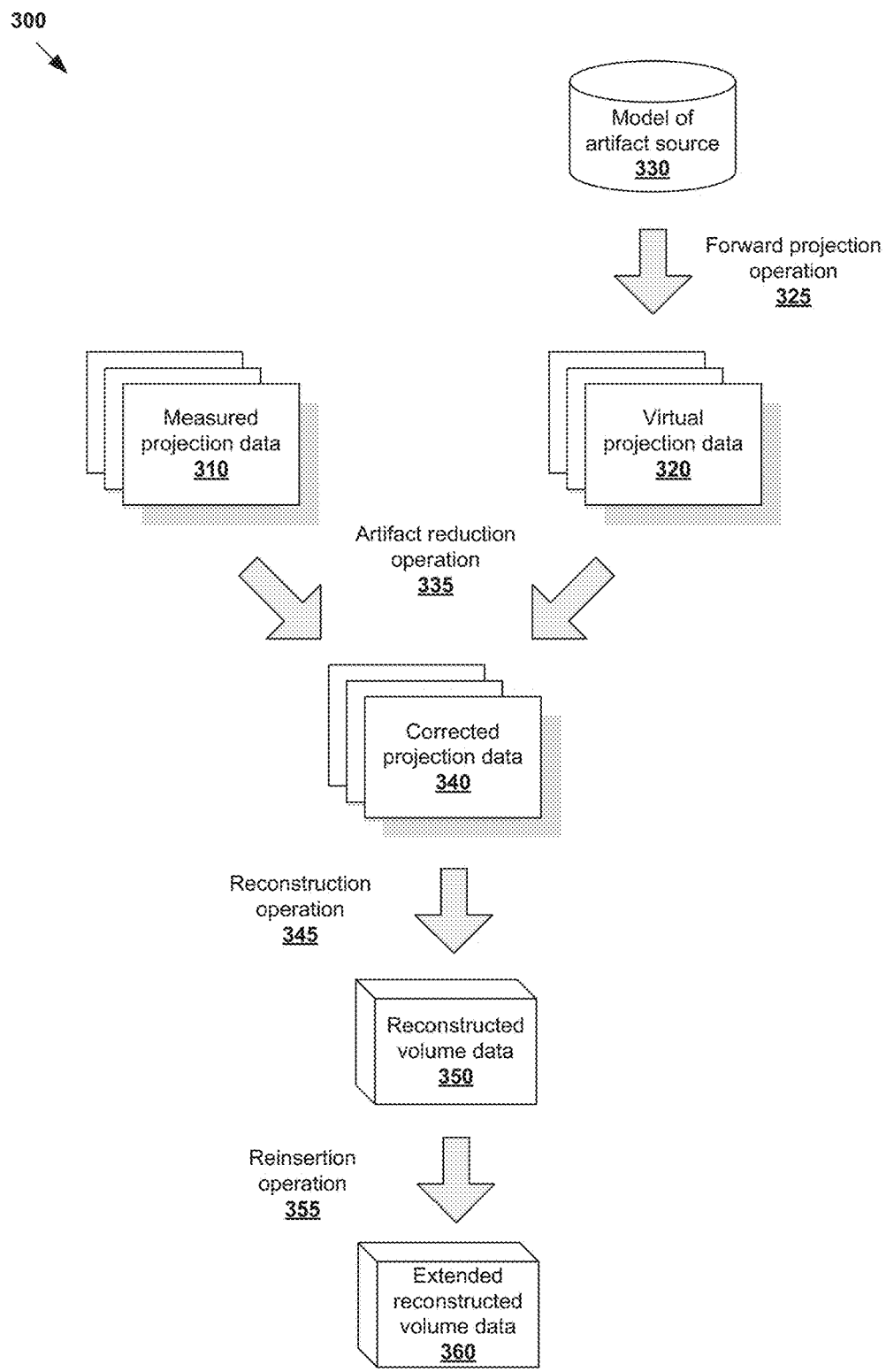
FIG. 3 is a flowchart of an example process to reduce image artifacts in reconstructed volume data.

FIG. 3 is a flowchart of example process 300 to reduce image artifacts in reconstructed volume data 350. Example process 300 may include one or more operations, functions, or actions illustrated by one or more blocks, such as 310 to 360. The various blocks may be combined into fewer blocks, divided into additional blocks, and/or eliminated based upon the desired implementation. Operations 325, 335, 345 and 355 in FIG. 3 may be performed by the computing device 170 of FIG. 1, and/or any other device not shown in FIG. 1.

Referring to 310 in FIG. 3, measured projection data 310 associated with target object 105 and an artifact source is obtained. As explained using FIG. 1, the artifact source may be treatment couch 210, couch rails 215, immobilization device 220, localization device 230, implant device 235, etc. Here, the term "obtained" or "obtain" may refer to either receiving measured projection data 310 (e.g., from controller 160) or retrieving it from a storage device. Measured projection data 310, which is acquired using radiation source 110 and detector 120 of imaging system 100, may be pre-processed after acquisition using imaging system 100. Any suitable pre-processing may be performed depending on the desired implementation, such as defect pixel correction, dark field correction, conversion from transmission integrals into attenuation integrals (e.g., log normalization with air norm), scatter correction, beam hardening correction, decimation, etc.

Referring to 320 and 330 in FIG. 3, virtual projection data 320 associated with the artifact source is generated based on model 330 of the artifact source. Here, the term "model" may refer generally to a representation of one or more physical properties of the artifact source. For example, model 330 may include a virtual representation of the position, orientation, shape, size, material (e.g., density), attenuation coefficient and electron density of the artifact source. Model 330 may be used to estimate artifacts caused by radiation beam from radiation source 110 travelling through the artifact source or part of the artifact source outside the imaging field 250.

Any suitable approach may be used to generate virtual projection data 320, such as forward projection operation 325 in FIG. 3 to forward-project model 330 of the artifact source. As used herein, "forward projection" may refer generally to a transformation from the volume space to the projection space. Forward projection (also known as synthesizing projection data) may include data such as attenuation path integrals (primary signal), Rayleigh scatter and Compton scatter. Forward projection operation 325 may be monochromatic or polychromatic; source-driven or destination-drive; voxel-based or blob-based; and use Ray Tracing, Monte Carlo or any suitable finite element methods.

Referring to 340 in FIG. 3, corrected projection data 340 is generated based on measured projection data 310 and virtual projection data 320. In one example, virtual projection data 320 is removed from measured projection data 310 to generate corrected projection data 340 using artifact reduction operation 335. Here, the term "removing" or "remove" at 340 in FIG. 3 may refer generally to a reduction of the visual impact of the artifact source and may result in partial or complete elimination of the artifact source from measured projection data 310.

For example, when the artifact source (e.g., implant device 235 or treatment couch 210) is at least partially within imaging field 250 (see also 260 and 261 in FIG. 2), corrected projection data 340 may be generated to fully or partially remove the artifact source from measured projection data 310 and/or to reduce or correct errors caused by the artifact source in measured projection data 310. In case of partial elimination, parts of the artifact source that exceeds imaging field 250 may be removed, while other parts within imaging field 250 are retained. In another example, when the artifact source (e.g., couch rails 215) is outside of imaging field 250 (see also 262 in FIG. 2), corrected projection data 340 may be generated to reduce or correct errors caused by the artifact source. As discussed, the "errors" are caused by the artifact source in the projection space and may include data inconsistencies, missing data, scatter, beam hardening, etc. Such errors lead to image artifacts in the volume space.

Referring to 350 in FIG. 3, reconstructed volume data 350 associated with target object 105 is generated from corrected projection data 340 by performing reconstruction operation 345. Any suitable reconstruction algorithm may be used, such as non-iterative reconstruction (e.g., filtered back projection), iterative reconstruction (e.g., algebraic and statistical based reconstruction), etc.

As such, using example process 300, corrected projection data 340 is able to account for the artifact source with model 330, and image artifacts caused by an artifact source in reconstructed volume data 350 may be reduced or removed.

According to example process 300, reconstructed volume data 350 may be somewhere between "assuming all of the artifacts are present" and "assuming all of the artifacts are removed." The artifacts caused by the artifact source may include truncation artifact as discussed above; motion artifact if the artifact source moves during scanning; or beam hardening and scatter. In the event of a truncation, model 330 of the artifact source provides additional data to facilitate the removal of the truncated artifact source.

In order to get a more complete or extended representation of the imaged volume, the artifact source may be reinserted after the reconstruction. For example, reinsertion operation 355 may be performed to reinsert model 330 into reconstructed volume data 350 to generate extended reconstructed volume data 360. Compared to reconstructed volume data 350, extended reconstructed volume data 360 includes reconstructions of both target object 105 and the artifact source and may extend imaging field 250 of imaging system 100. Extended reconstructed volume data 360 may have the same size as reconstructed volume data 350. Reinsertion operation 355 may be useful for applications (e.g., dose verification, etc.) that require information outside of imaging field 250. For some applications, however, reinsertion operation 355 may not be necessary, such as if the artifact source is outside of imaging field 250.

Example process 300 may be used for the correction of artifacts in volume data reconstructed from any suitable projection data, such as CBCT images. In the following, various examples will be further described with reference to FIG. 4 (with position and orientation estimation), FIG. 5 (with trajectory estimation) and FIG. 6 (with model extraction). Example projection data and reconstructed volume data will be explained using FIG. 7, FIG. 8A, FIG. 8B, FIG. 8C and FIG. 8D; and example computing device 170 using FIG. 9.

Position and Orientation Estimation

Model 330 in FIG. 3 relies on some prior knowledge on the position and orientation of the artifact source in order to generate virtual projection data 320. For example, treatment couch 210, couch rails 215, immobilization device 220 and any other device attached to imaging system 100 each have a known position and orientation. This allows virtual projection data 320 to be directly computed from model 330 in order to remove the artifact source and to reduce artifacts from measured projection data 310.

Figure 4:
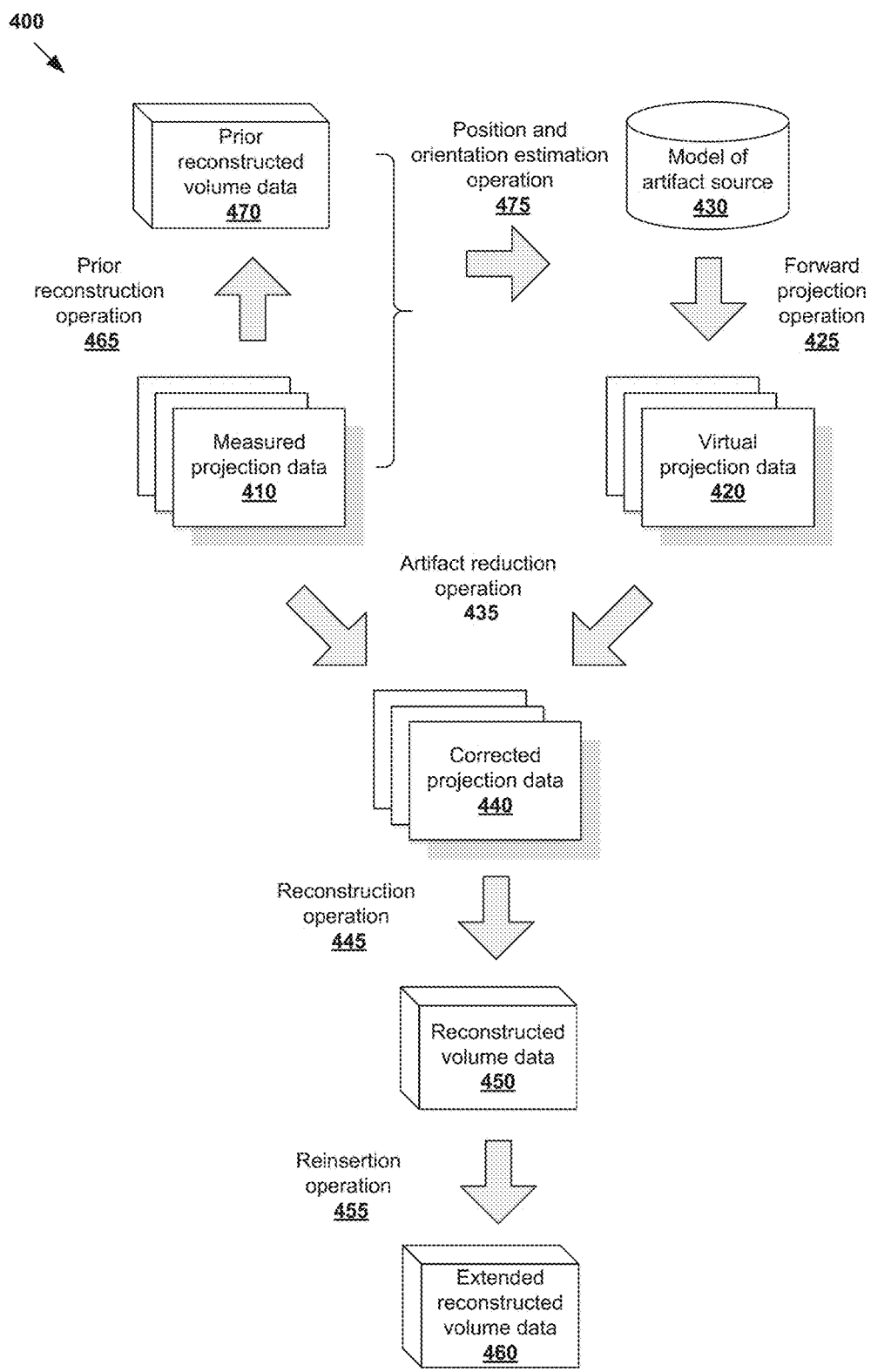
FIG. 4 is a flowchart of an example process with position and orientation estimation to reduce image artifacts in reconstructed volume data.

However, for an artifact source with unknown position and orientation, its position and orientation may be estimated before virtual projection data 320 is generated. In more detail, FIG. 4 is a flowchart of example process 400 with position and orientation estimation to reduce image artifacts in reconstructed volume data 450. Example process 400 may include one or more operations, functions, or actions illustrated by one or more blocks, such as 410 to 475. Computing device 170 in FIG. 1, or any other suitable device, may be used to implement example process 400.

Blocks 410 to 460 in FIG. 4 are similar to corresponding blocks 310 to 360 in FIG. 3. Similar to 310, 320, 325 and 330 in FIG. 3, measured projection data 410 in FIG. 4 is acquired using imaging system 100 and virtual projection data 420 generated based on model 430 of an artifact source by performing forward projection operation 425. Similar to 335, 340, 350, 355 and 360 in FIG. 3, artifact reduction operation 435, reconstruction operation 445 and reinsertion operation 455 in FIG. 4 are performed to generate corrected projection data 440, reconstructed volume data 450 and extended reconstructed volume data 460, respectively.

Additionally, one example of position and orientation estimation is shown at 465 and 470 in FIG. 4. In particular, prior reconstructed volume data 470 may be generated from measured projection data 410 by performing prior reconstruction operation 465. Here, the term "prior" in "prior reconstruction operation" 465 represents a preliminary operation on measured projection data 410 that is performed before artifact reduction operation 435, reconstruction operation 445 and reinsertion operation 455. Any suitable reconstruction algorithm may be used to perform prior reconstruction operation 465, such as iterative and non-iterative reconstruction.

Next, referring to 475 in FIG. 4, measured projection data 410 and/or prior reconstructed volume data 470 may be used to estimate the position and orientation of the artifact source. Position and orientation estimation operation 475 may include locating the artifact source within a two-dimensional or three-dimensional space. This may include registering model 430 of the artifact source to measured projection data 410 (i.e., two-dimensional image registration) and/or prior reconstructed volume data 470 (i.e., three-dimensional image registration).

Any suitable approach may be used, such as feature point detection, object recognition, rigid registration, non-rigid image registration, etc. For example, features associated with an artifact source may be detected in measured projection data 410 and/or prior reconstructed volume data 470. The detected features are then matched with model 430 to determine the position and orientation of the artifact source. The features may be two-dimensional or three-dimensional. Object recognition may also be performed to identify the type of artifact source based on the detected features, such as specific immobilization device 220 worn by target object 105.

Further, image registration may be used to transform prior reconstructed volume data 470 and/or measured projection data 410 into a reference coordinate system of model 430. Rigid registration includes linear transformations, such as translation and rotation. Non-rigid registration is more suitable for artifact sources that are deformable by, for example, target object 105 during scanning. For example, non-rigid registration may include affine and scaling transformations, locally diverse transformations, or iterative optimization of an objective function that models the similarity between model 430 on the one hand, and measured projection data 410 and/or prior reconstructed volume data 470 on the other hand.

As an example, although model 430 of a head frame worn by target object 105 is available, the actual position and orientation of the head frame may not be known until scanning is performed. In this case, model 430 of the head frame cannot be used directly to generate virtual projection data 420. To estimate its position and orientation of the head frame, its model 430 is registered in measured projection data 410 and/or prior reconstructed volume data 470. Based on the estimated position and orientation, virtual projection data 420 is generated from model 430 of the head frame.

Although an example is shown in FIG. 4, position and orientation estimation may also be performed on measured projection data 410 using two-dimensional to two-dimensional (2D-2D) or two-dimensional to three-dimensional (2D-3D) registration algorithms. In this case the prior reconstructed volume data 470 are not required. Any additional or alternative estimation approaches may be used.

Trajectory Estimation

As discussed using FIG. 2, motion artifacts may be caused any artifact source that moves during scanning. For example, treatment couch 210 (e.g., in a couch tracking mode) and localization device 230 (e.g., marker block) may not be completely stationary during scanning. To reduce such motion artifacts, the trajectory of the artifact source may be estimated and time-dependent virtual projection data synthesized.

Figure 5:
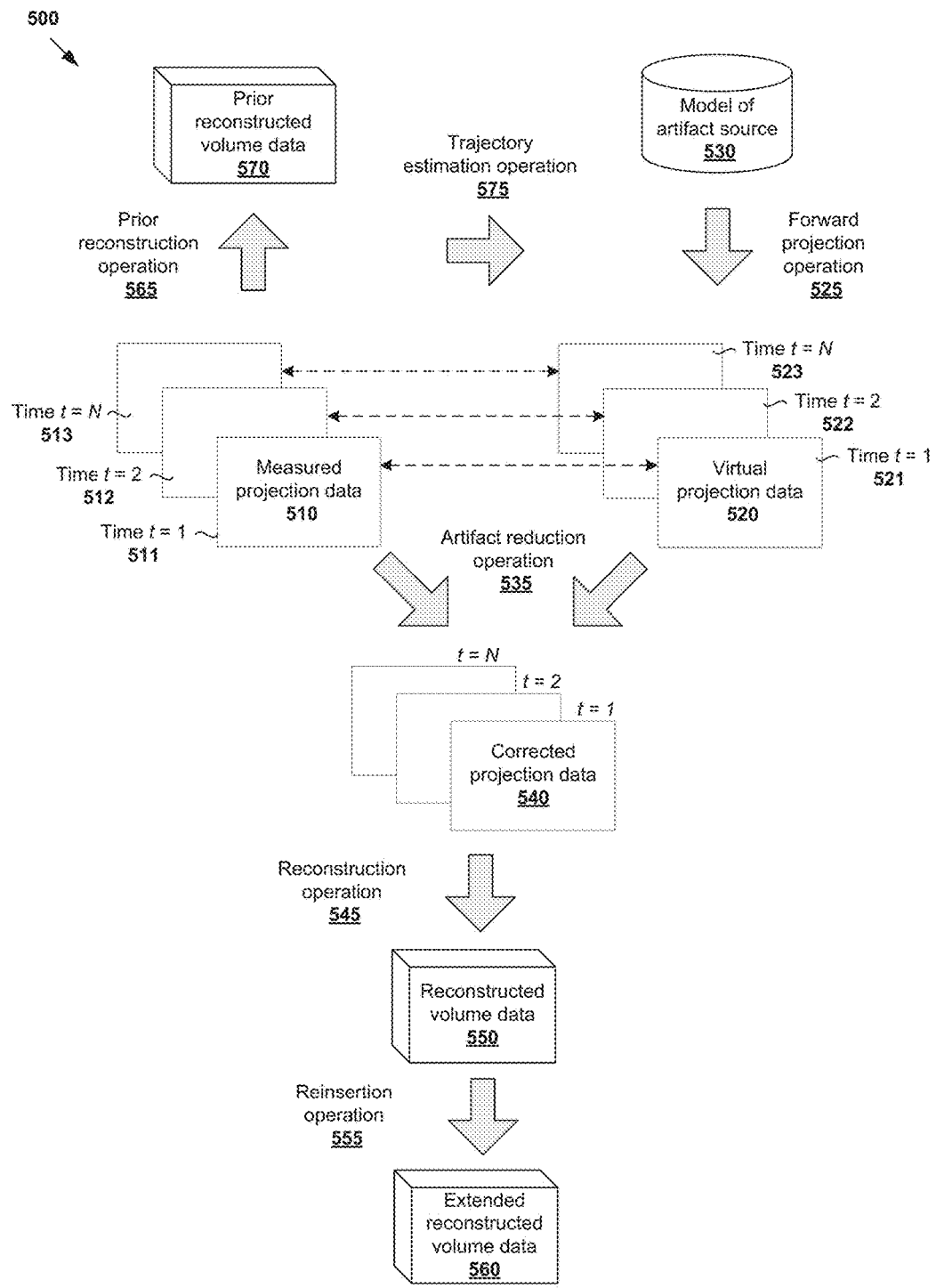
FIG. 5 is a flowchart of an example process with trajectory estimation to reduce image artifacts in reconstructed volume data.

In more detail, FIG. 5 is a flowchart of example process 500 with trajectory estimation to reduce image artifacts in reconstructed volume data 550. Example process 500 may include one or more operations, functions, or actions illustrated by one or more blocks, such as 510 to 575. Computing device 170 in FIG. 1, or any other suitable device, may be used to implement example process 500. Blocks 510 to 560 in FIG. 5 are similar to corresponding blocks 310 to 360 in FIG. 3.

In particular, similar to 310, 320, 325 and 330 in FIG. 3, measured projection data 510 in FIG. 5 is acquired using imaging system 100 and virtual projection data 520 generated based on model 530 of an artifact source by performing forward projection operation 525. Similar to 335, 340, 350, 355 and 360 in FIG. 3, artifact reduction operation 535, reconstruction operation 545 and reinsertion operation 555 in FIG. 5 are performed to generate corrected projection data 540, reconstructed volume data 550 and extended reconstructed volume data 560, respectively.

Additionally, referring to 565 and 570 in FIG. 5, prior reconstructed volume data 570 is generated from measured projection data 510 by performing prior reconstruction operation 565. Prior reconstruction operation 565 represents a preliminary operation on measured projection data 510 that is performed before artifact reduction operation 535, reconstruction operation 545 and reinsertion operation 555. Any suitable reconstruction algorithm may be used, such as iterative and non-iterative reconstruction.

To reduce motion artifacts, trajectory estimation operation 575 is performed to estimate a trajectory of the artifact source from an initial position to an end position. In this case, measured projection data 510 may represent a time series of measured projection images taken over time, such as at time t=1, 2 . . . N. See 511, 512 and 513 where three images are shown for simplicity. The position of the artifact source at time t=1 may be taken as the initial position, and its position at t=N as the end position.

In one example, trajectory estimation operation 575 may include estimating the initial position of the artifact source at time t=1 based on prior reconstructed volume data 570. Next, motion of the artifact source over time may be extracted from measured projection data 510 by tracking its positional change from the initial position at t=1 (see 511) to the end position at t=N (see 513). Any suitable tracking approach may be used, such as kernel-based tracking, point tracking, silhouette tracking, model-based pose estimation, etc. If available, a motion model of the artifact source may be used, such as whether the artifact source is likely to undergo translation, rotation, affine or a non-rigid motion.

Although an example is shown in FIG. 5, the trajectory of the artifact source may be determined based on an external source. For example, localization device 230 (see FIG. 2) such as a Calypso system may be used to assist with trajectory estimation. Any other localization device 230 may be used, such as VisionRT or any suitable camera system. This is generally useful to reduce motion artifacts introduced by moving markers, such as fiducial markers that are attached to or implanted in target object 105. The fiducial markers are generally used to define points or landmarks of a region of interest of target object 105 such as a tumor. When target object 105 moves during scanning (e.g., due to respiratory motion, cardiac motion, body motion, etc.), the fiducial markers also move and cause motion artifacts in measured projection data 510. For tumor localization, multiple beacons (e.g., two or three) may be placed around the tumor to send data (e.g., position and orientation data) to the Calypso system wirelessly. The data may then be used to determine the trajectory of the moving fiducial markers to address motion artifacts.

Virtual projection data 520 may then be generated based on the trajectory estimated using trajectory estimation operation 575 and model 530 of the artifact source. In this case, virtual projection data 520 is generated to represent a time series of virtual projection images at t=1, 2 . . . N. For example, virtual projection images 521, 522 and 523 represent various positions of the artifact source from an initial position at t=1, an intermediate position at t=2 to an end position at t=N.

Corrected projection data 540 may then be generated from virtual projection data 520 using artifact reduction operation 535. In particular, virtual projection images 521, 522 and 523 are used to correct corresponding measured projection images 511, 512 and 513 separately. For example, for t=1, virtual projection image 521 is used to correct measured projection image 511. For t=2, virtual projection image 522 is used to correct measured projection image 512, and finally for t=N, virtual projection image 523 is used to correct measured projection image 513.

Since artifact reduction operation 535 is performed on the various projection images, example process 500 may be used independent of the scan type (e.g., three-dimensional or four-dimensional). Reconstructed volume data 550 generated from corrected projection data 540 will also have reduced motion artifacts caused by the artifact source. In practice, however, motion artifacts induced by moving patient tissue might still be present.

Model Extraction

The examples in FIG. 3, FIG. 4 and FIG. 5 rely on a known model 330/430/530 of the artifact source for artifact reduction. Where there is no model is available, model extraction may be performed using example process 600 in FIG. 6. For example, when a model of treatment couch 210 or immobilization device 220 is not available, the model may be extracted to suppress streaking artifacts in respiratory-correlated image reconstructions.

Figure 6:
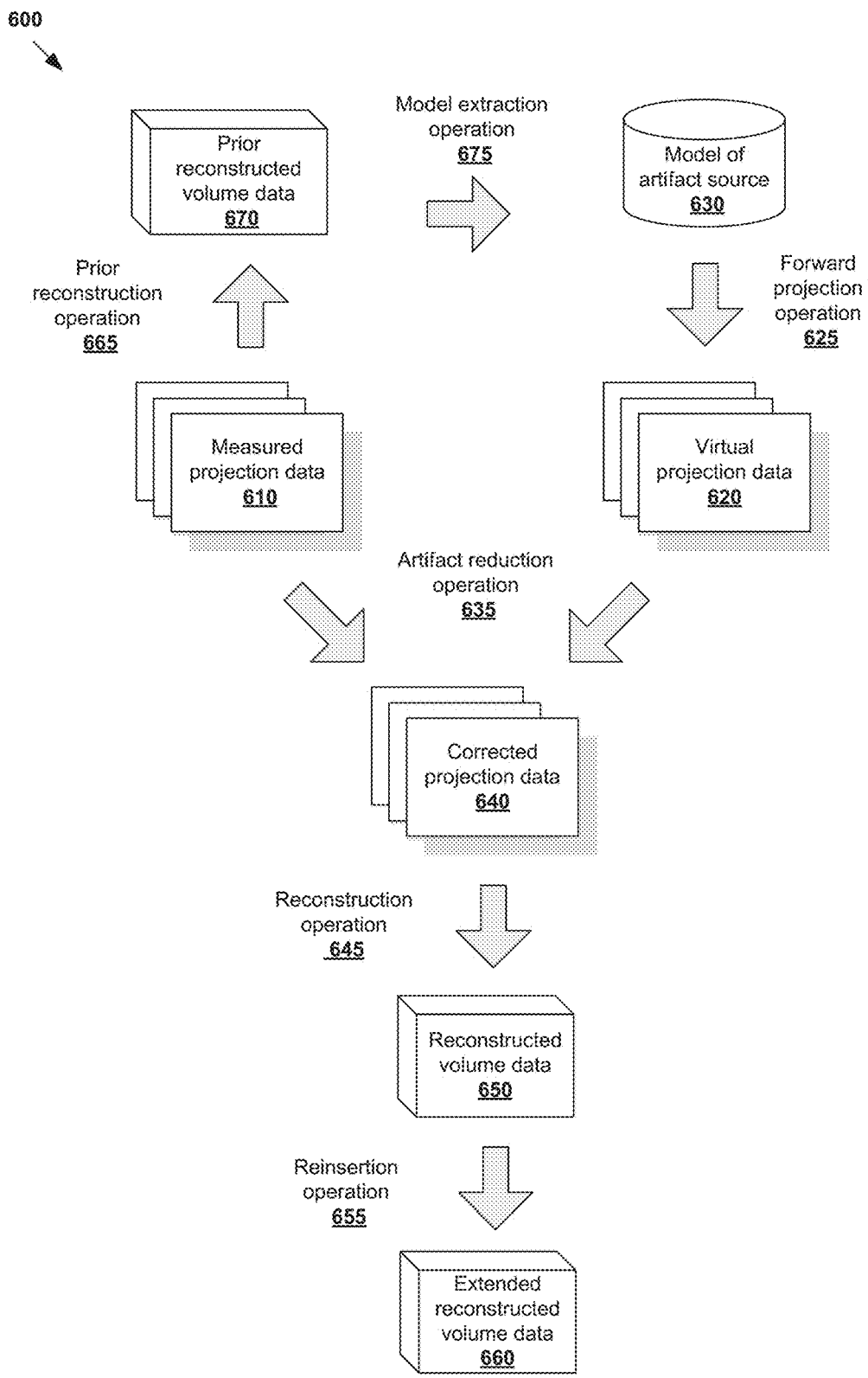
FIG. 6 a flowchart of an example process with model extraction to reduce image artifacts in reconstructed volume data.

In more detail, FIG. 6 is a flowchart of example process 600 with model extraction to reduce image artifacts in reconstructed volume data 650. Example process 600 may include one or more operations, functions, or actions illustrated by one or more blocks, such as 610 to 675. Computing device 170 in FIG. 1, or any other suitable device, may be used to implement example process 600. Blocks 610 to 660 in FIG. 6 are similar to corresponding blocks 310 to 360 in FIG. 3.

In particular, similar to 310, 320, 325 and 330 in FIG. 3, measured projection data 610 in FIG. 6 is acquired using imaging system 100 and virtual projection data 620 generated based on model 630 of an artifact source by performing forward projection operation 625. Similar to 335, 340, 350, 355 and 360 in FIG. 3, artifact reduction operation 635, reconstruction operation 645 and reinsertion operation 655 in FIG. 6 are performed to generate corrected projection data 640, reconstructed volume data 650 and extended reconstructed volume data 660, respectively.

Additionally, referring to 665 and 670 in FIG. 6, prior reconstructed volume data 670 is generated from measured projection data 610 by performing prior reconstruction operation 665 using any suitable reconstruction algorithm (e.g., iterative and non-iterative reconstruction). Prior reconstruction operation 665 represents a preliminary operation on measured projection data 610 that is performed before artifact reduction operation 635, reconstruction operation 645 and reinsertion operation 655.

Model extraction operation 675 is performed to determine model 630 of the artifact source. In one example, information from prior reconstructed volume data 670 may be utilized to extract model 630 of an artifact source that is present within radiation field 240 during scanning. As discussed using FIG. 2 and FIG. 3, the artifact source may be (a) fully within, (b) partially within or (c) outside of imaging field 250. A voxel-based model extraction may be used to segment prior reconstructed volume data 670 into patient voxels and non-patient voxels. The patient voxels ("first voxels") represent a first region within a body outline of target object 105 while the non-patient voxels ("second voxels") represent a second region outside of the body outline. Non-patient voxels may also be inside the body outline, such as voxels relating to implant device 235, etc. To obtain model 630 of the artifact source (representing the second region), patient voxels in the first region may be removed from prior reconstructed volume data 670.

In some cases, the segmentation may rely on several assumptions. For example, since target object 105 is usually positioned substantially in the middle of imaging field 250, central voxels are assumed to be patient voxels. On the other hand, corners of prior reconstructed volume data 670 are usually non-patient voxels. Any suitable approach may be used for the segmentation, such as threshold-based initial mask estimation, erosion of initial mask estimation, two-pass flood fill, dilation of flood fill result, etc. Dilation and erosion techniques can generally help to remove noise and gaps at the boundary of the region. Depending on the desired implementation, a more robust or sophisticated shape-based or atlas-based segmentations may be used in practice. Also, the assumptions discussed here may not hold true for certain cases, such as when an implant is placed next to a tumor that is present in the middle of imaging field 250.

Although not shown in FIG. 6, feature point detection, object recognition and object modelling approaches may be used to generate model 630. A combination is also possible with example process 500 for removing moving artifact source.

Example Implementations

Figure 7:
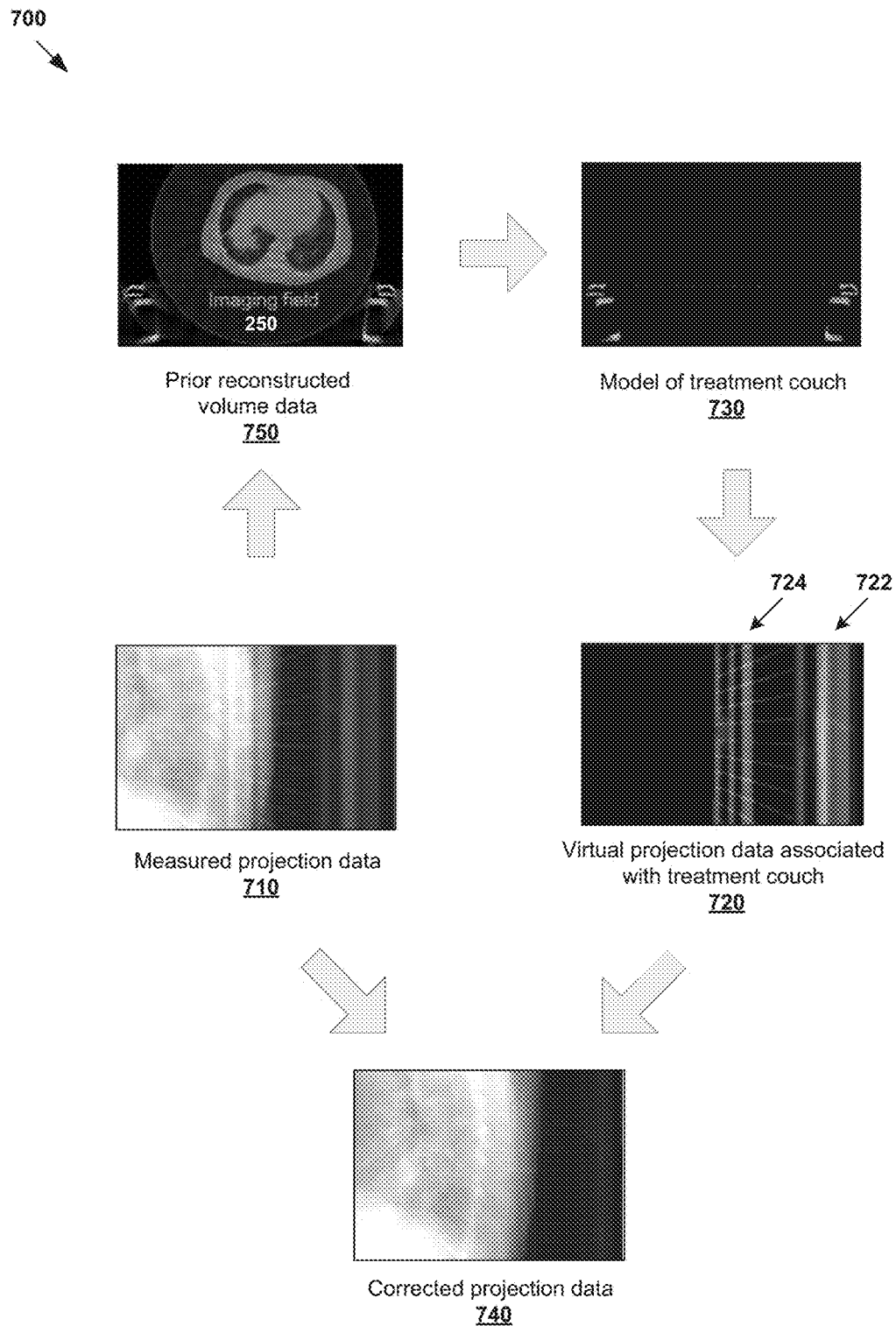
FIG. 7 illustrates an example implementation of image artifact reduction according to the examples in FIG. 3, FIG. 4, FIG. 5 and FIG. 6.

FIG. 7 illustrates an example implementation of artifact reduction according to the examples in FIG. 3, FIG. 4, FIG. 5 and FIG. 6. Although treatment couch 210 is used as an example artifact source for projection-based couch removal, it will be appreciated any other artifact source may be used. In more detail, measured projection data 710 (e.g., CBCT images) includes projection data of target object 105 (e.g., patient) and treatment couch 210 that is truncated due to not being fully visible within imaging field 250.

To reduce image artifacts in the volume data reconstructed from measured projection data 710, virtual projection data 720 of treatment couch 210 is generated by forward projecting model 730 of treatment couch 210. 722 and 724 in FIG. 7 represent attenuation path integrals of treatment couch 210. Corrected projection data 740 is then generated by using measured projection data 710 and virtual projection data 720 to at least partially remove treatment couch 210.

FIG. 7 also shows an example representation of prior reconstructed volume data 750 (a 2D slice of the 3D volume data is shown for simplicity) generated from measured projection data 710. Prior reconstructed volume data 750 may be generated for position and orientation estimation according to example process 400 in FIG. 4, trajectory estimation according to example process 500 in FIG. 5 and model extraction according to example process 600 in FIG. 6.

Prior reconstructed volume 750 also shows the truncation of treatment couch 210, which is only partially visible within imaging field 250. Using the example in FIG. 6, model 730 of treatment couch 210 may be extracted from prior reconstructed volume data 750, such as based on segmented body outline of target object and threshold segmentation for artifact suppression.

Figure 8A:
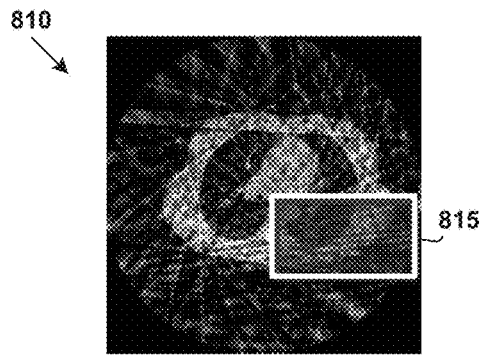
FIG. 8A illustrates example reconstructed volume data generated by applying a reconstructed operation on measured projection data in FIG. 7.
Figure 8B:
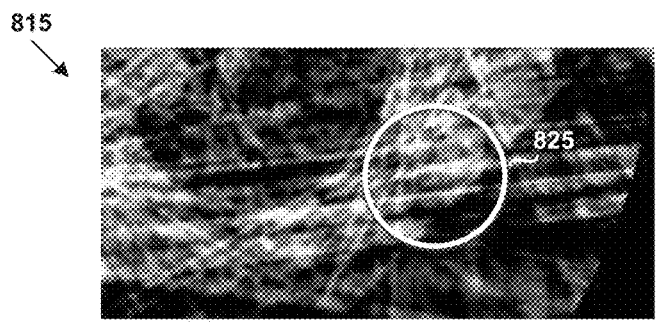
FIG. 8B illustrates an enlarged section of the reconstructed volume data in FIG. 8A.
Figure 8C:
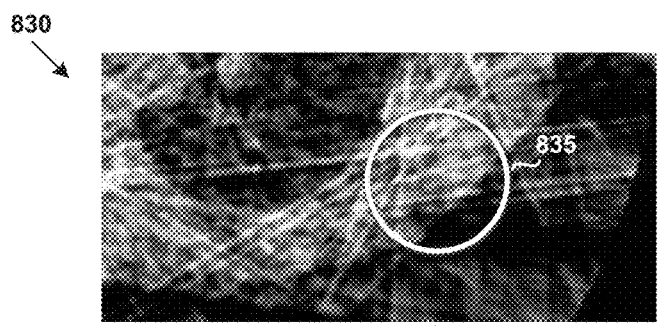
FIG. 8C illustrates example reconstructed volume data generated by applying a reconstructed operation on corrected projection data in FIG. 7.
Figure 8D:
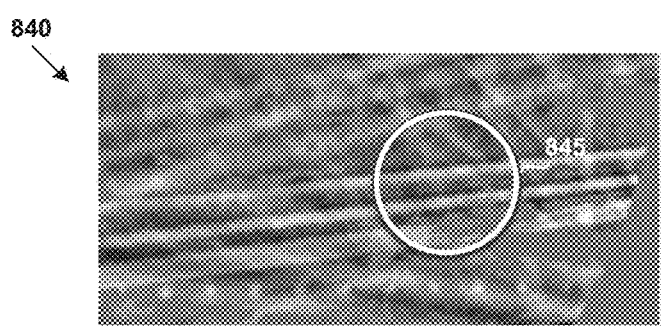
FIG. 8D illustrates a difference between the example reconstructed volume data in FIG. 8A and the example reconstructed volume data in FIG. 8C.

Further examples are provided in FIG. 8A, FIG. 8B, FIG. 8C and FIG. 8D. In more detail, FIG. 8A illustrates example reconstructed volume data 810 generated by applying a reconstruction operation on measured projection data 710 in FIG. 7. FIG. 8B illustrates enlarged section 815 of reconstructed volume data 810 in FIG. 8A. FIG. 8C illustrates example reconstructed volume data 830 generated by applying a reconstruction operation on corrected projection data 740 in FIG. 7. FIG. 8D illustrates difference 840 between example reconstructed volume data 810 in FIG. 8A and example reconstructed volume data 830 in FIG. 8C. Here, the reconstruction of measured projection data 710 in FIG. 8A and corrected projection data 740 may be performed using any suitable reconstruction operation (e.g., 345/445/545/645 in FIGS. 3-6), such as a respiratory-correlated four-dimensional (4D) image reconstruction.

Various image artifacts (e.g., streaking artifacts due to poor data sampling as a result of respiratory-correlated 4D image reconstruction) are observed in FIG. 8B, such as in highlighted area 825. By removing treatment couch data 720 from measured projection data 710, the image artifacts (e.g., streaking/sampling) related to treatment couch 210 are consequently removed from reconstructed volume data 830. The image artifacts reduced may be observed in reconstructed volume data 830 in FIG. 8C, such as in corresponding highlighted area 835. The artifact reduction is also represented in FIG. 8D.

Examples in the present disclosure may be used in conjunction with other approaches for further artifact reduction, such as respiratory and/or cardiac motion compensation, motion updates (e.g., McKinnon-Bates (MKB) algorithms), etc.

Computing Device

Figure 9:
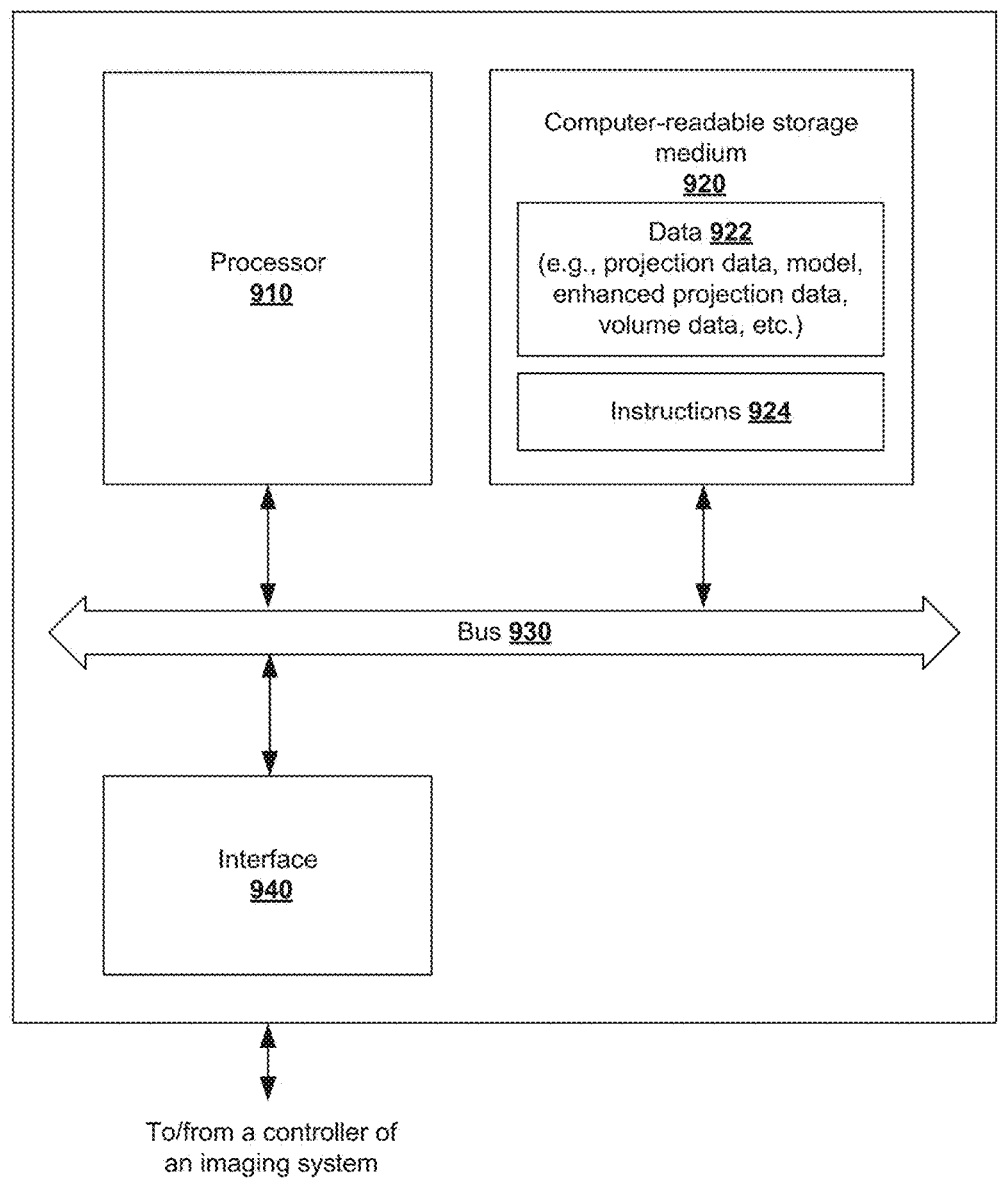
FIG. 9 is an example computing device configured to reduce image artifacts in reconstructed volume data.

The above examples can be implemented by hardware, software or firmware or a combination thereof. FIG. 9 is a schematic diagram of an example computing device 900/170 to reduce artifact in projection data acquired using imaging system 100. Example computing device 900/170 may include processor 910, computer-readable storage medium 920, interface 940 to interface with controller 160 of imaging system 100, and bus 930 that facilitates communication among these illustrated components and other components. Processor 910 is to perform processes described herein with reference to FIG. 1 to FIG. 8D.

Computer-readable storage medium 920 may store any suitable data 922, such as measured projection data 310/410/510/610, model of artifact sources 330/430/530/630, virtual projection data 320/420/520/620, corrected virtual projection data 340/440/540/640, reconstructed volume data 350/450/550/650, prior reconstructed volume data 470/570/670, extended volume data 360/460/560/660, etc. Computer-readable storage medium 920 may further store computer-readable instructions 924 which, in response to execution by processor 910, cause processor 910 to perform processes described herein with reference to FIG. 1 to FIG. 8D.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof.

Those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure.

We claim:

1. A method to reduce image artifacts, the method comprising:
    obtaining measured projection data acquired using an imaging system, wherein the measured projection data comprises a time series of measured projection images at times t=1, 2 . . . N, wherein N>2, the measured projection images including a target object and an artifact source within a radiation field of the imaging system;
    reconstructing the measured projection data into prior reconstructed volume data;
    estimating a trajectory of the artifact source from an initial position at the time t=1 to an end position at the time t=N based on the measured projection data and the prior reconstructed volume data;
    forward projecting a model representing one or more physical properties of the artifact source to generate virtual projection data associated with the artifact source based on the model and the estimated trajectory of the artifact source, wherein the model is generated independently from reconstructing the measured projection data, wherein the virtual projection data associated with the artifact source is different from the measured projection data associated with the artifact source, and wherein the virtual projection data comprises a time series of virtual projection images including the artifact source at the times t=1, 2 . . . N;
    generating corrected projection data based on the measured projection data and the virtual projection data by subtracting each of the virtual projection images at the times t=1, 2 . . . N from the corresponding measured projection images at the times t=1, 2 . . . N based on the estimated trajectory of the artifact source; and
    reconstructing the corrected projection data into reconstructed volume image data to reduce image artifacts caused by the artifact source.

2. The method of claim 1, wherein the artifact source is at least partially within an imaging field that is smaller than the radiation field and the corrected projection data is generated partially based on the virtual projection data to at least partially remove the artifact source from the measured projection data, to reduce errors caused by the artifact source in the measured projection data, or to partially remove the artifact source from the measured projection data and reduce errors caused by the artifact source in the measured projection data.

3. The method of claim 1, wherein the artifact source is outside of an imaging field that is smaller than the radiation field and the corrected projection data is generated partially based on the virtual projection data to reduce errors caused by the artifact source in the measured projection data.

4. The method of claim 1, further comprising reinserting the model of the artifact source into the reconstructed volume data to generate extended volume image data associated with the target object and artifact source.

5. An imaging system configured to reduce artifact in projection data, comprising:
    a radiation source;
    a detector;
    a controller; and
    a computing device, including a processor, coupled to the controller, wherein the processor is configured to:
        obtain measured projection data acquired using the imaging system, wherein the measured projection data comprises a time series of measured projection images at times t=1, 2 . . . N, wherein N>2, the measured projection images including a target object and an artifact source within a radiation field of the imaging system;
        reconstruct the measured projection data into prior reconstructed volume data;
        estimate a trajectory of the artifact source from an initial position at the time t=1 to an end position at the time t=N based on the measured projection data and the prior reconstructed volume data;
        forward project a model representing one or more physical properties of the artifact source to generate virtual projection data associated with the artifact source based on the model and the estimated trajectory of the artifact source, wherein the model is generated independently from reconstructing the measured projection data, wherein the virtual projection data associated with the artifact source is different from the measured projection data associated with the artifact source, and wherein the virtual projection data comprises a time series of virtual projection images including the artifact source at the times t=1, 2 . . . N;
        generate corrected projection data based on the measured projection data and the virtual projection data by subtracting each of the virtual projection images at the times t=1, 2 . . . N from the corresponding measured projection images at the times t=1, 2 . . . N based on the estimated trajectory of the artifact source; and
        reconstruct the corrected projection data into reconstructed volume image data to reduce image artifacts caused by the artifact source.

6. The imaging system of claim 5, wherein the artifact source is at least partially within an imaging field that is smaller than the radiation field and the corrected projection data is generated partially based on the virtual projection data to at least partially remove the artifact source from the measured projection data, to reduce errors caused by the artifact source in the measured projection data, or to partially remove the artifact source from the measured projection data and reduce errors caused by the artifact source in the measured projection data.

7. The imaging system of claim 5, wherein the artifact source is outside of an imaging field that is smaller than the radiation field and the corrected projection data is generated partially based on the virtual projection data to reduce errors caused by the artifact source in the measured projection data.

8. The imaging system of claim 5, wherein the processor is further configured to reinsert the model of the artifact source into the reconstructed volume data to generate extended volume image data associated with the target object and artifact source.

9. A non-transitory computer-readable storage medium that includes a set of instructions which, in response to execution by a processor of a computing device, cause the processor to perform a method to reduce image artifacts, the method comprising:

obtaining measured projection data acquired using an imaging system, wherein the measured projection data comprises a time series of measured projection images at times t=1, 2 N, wherein N>2, the measured projection images including a target object and an artifact source within a radiation field of the imaging system;

reconstructing the measured projection data into prior reconstructed volume data;

estimating a trajectory of the artifact source from an initial position at the time t=1 to an end position at the time t=N based on the measured projection data and the prior reconstructed volume data;

forward projecting a model representing one or more physical properties of the artifact source to generate virtual projection data associated with the artifact source based on the model and the estimated trajectory of the artifact source, wherein the model is generated independently from reconstructing the measured projection data, wherein the virtual projection data associated with the artifact source is different from the measured projection data associated with the artifact source, and wherein the virtual projection data comprises a time series of virtual projection images including the artifact source at the times t=1, 2 . . . N;

generating corrected projection data based on the measured projection data and the virtual projection data by subtracting each of the virtual projection images at the times t=1, 2 . . . N from the corresponding measured projection images at the times t=1, 2 . . . N based on the estimated trajectory of the artifact source; and reconstructing the corrected projection data into reconstructed volume image data to reduce image artifacts caused by the artifact source.

* * * * *